United States Patent [19]

George et al.

[11] 4,348,280

[45] Sep. 7, 1982

[54] PROPORTIONING DIALYSIS MACHINE

[75] Inventors: Richard W. George, Libertyville; William J. Schnell, Arlington Heights, both of Ill.

[73] Assignee: Baxter Travenol Laboratories, Inc., Deerfield, Ill.

[21] Appl. No.: 126,404

[22] Filed: Mar. 3, 1980

Related U.S. Application Data

[63] Continuation of Ser. No. 750,028, Dec. 13, 1976, abandoned, which is a continuation of Ser. No. 654,137, Jan. 30, 1976, abandoned, which is a continuation-in-part of Ser. No. 516,526, Oct. 21, 1974, abandoned.

[51] Int. Cl.³ .................. B01D 31/00; A61M 1/00
[52] U.S. Cl. .................. 210/101; 55/165; 210/104; 210/127; 210/134; 210/136; 210/137; 210/188; 210/321.3
[58] Field of Search .......... 55/165; 210/321.3, 101, 210/104, 127, 134, 136, 188, 137, 646, 647

[56] References Cited

U.S. PATENT DOCUMENTS

| | | | |
|---|---|---|---|
| 1,910,088 | 5/1933 | Cherry | 55/165 |
| 2,457,903 | 1/1949 | Kantor et al. | 55/165 |
| 3,474,907 | 10/1969 | Cary et al. | 210/321 B X |
| 3,528,550 | 9/1970 | Cappelen, Jr. | 210/321 B X |
| 3,563,381 | 2/1971 | Edelson et al. | 210/321 B X |
| 3,827,561 | 8/1974 | Serfass et al. | 210/321 B X |
| 3,878,095 | 4/1975 | Frasier et al. | 210/321 B X |

FOREIGN PATENT DOCUMENTS

| | | | |
|---|---|---|---|
| 572818 | 2/1958 | Italy | 55/165 |
| 31-10142 | 11/1956 | Japan | 210/321.3 |
| 206804 | 4/1924 | United Kingdom | 55/165 |
| 215832 | 5/1924 | United Kingdom | 55/165 |
| 230160 | 3/1925 | United Kingdom | 55/165 |
| 297964 | 10/1928 | United Kingdom | 55/165 |
| 527204 | 10/1940 | United Kingdom | 55/165 |

*Primary Examiner*—Frank A. Spear, Jr.
*Attorney, Agent, or Firm*—Thomas R. Schuman; Gerald S. Geren

[57] ABSTRACT

An improved proportioning dialysis machine is disclosed herein. The machine includes an improved degassing system, dialysis solution flow rate and pressure control system, and sterilization system.

The degassing system includes a degassing chamber, a first pump for applying a negative pressure to said chamber and a second pump for drawing degassed water from the chamber. The dialysis solution flow rate and pressure control system includes a restriction upstream of a dialyzer, a restriction placed downstream of the dialyzer, and a pump positioned downstream of the downstream restriction. The two restrictions can be adjusted in relation to the pump so as to control the flow rate and pressure within the dialyzer. The sterilization system includes a heater and controls and a valve for recirculating heated water through the proportioning machine so as to sterilize the interior thereof.

13 Claims, 7 Drawing Figures

PROPORTIONING DIALYSIS MACHINE

CROSS REFERENCE TO RELATED APPLICATIONS

This application is a continuation of application, Ser. No. 750,028 filed Dec. 13, 1976; which is a continuation of application, Ser. No. 654,137 filed Jan. 30, 1976; which is a continuation-in-part of Ser. No. 516,526 filed Oct. 21, 1974, all now abandoned.

BACKGROUND OF THE INVENTION

This invention relates to artificial kidney systems; and more particularly, to a proportioningtype dialysis machine for use in such systems.

In an artificial kidney system, a dialysis machine delivers dialysis solution under carefully controlled conditions to a dialyzer or artificial kidney. There are two basic types of dialysis machines. One is known as a batch-type machine and the other is a proportioning or continuous feed machine.

In both types of machines dialysis concentrate is mixed with water to provide the dialysis solution which is delivered to the dialyzer. Both machines also include means for sterilizing the machine, a heater system for maintaining the dialysis solution at body or physiological temperature (about 37° C.), a device for removing gas and minimizing gas in the dialysis solution, and means for controlling the pressure and flow rate of the dialysis solution in the dialyzer. Furthermore in proportioning machines, provisions are also made for continuously preparing the dialysis solution by mixing or proportioning the water and dialysis concentrate and for controlling the composition of the dialysis solution.

Proportioning machines are generally more compact and smaller in size than the batch-type machine. For this reason, among others, the proportioning machines have experienced increased popularity.

Existing proportioning machines generally include the required gas removers, heaters, pressure controls, etc., but have been found to be deficient in certain respects. For example, one type of gas removal system, as shown in U.S. Pat. No. 3,738,382, includes a heater for heating the water to a high temperature and a debubbling chamber for removing gas from the heated water at atmospheric pressure. This system does not effectively degass the water and the heating of the water caused dissolved minerals to precipitate and clog passageways within the dialysis machine.

A second type of gas removal system is shown in U.S. Pat. No. 3,528,550. In this system water is fed to a degassing chamber which is maintained at a pressure below atmospheric pressure by a venturi through which dialysis solution flows. Thus the pressure in the degassing chamber is directly related to the dialysis solution flow rate through the venturi. The venturi only applies a moderate negative pressure to the degassing tank and thus does not effectively degass the water.

It is therefore an object of this invention to provide an effective degassing system, and particularly for use in a proportioning dialysis machine.

In the degassing system shown in U.S. Pat. No. 3,528,550, the degassing chamber pressure may vary with dialysis solution flow rate, which, in turn, may vary with dialysis conditions, such as patient size, etc. Variations in degassing chamber pressure may affect gas removal.

It is therefore an object of this invention to provide a degassing system which functions independently of the dialysis solution flow rates.

During dialysis it is desirable to control the dialysis solution pressure in the dialyzer. However, changes in the dialysis solution flow rate through the dialyzer cause the dialysis solution pressure to vary.

It is also an object of this invention to provide means for controlling the dialysis solution pressure in the dialyzer as the dialysis solution flow rate changes.

These and other objects of this invention will become apparent from the following description and appended claims.

SUMMARY OF THE INVENTION

There is provided by virtue of this invention a proportioning dialysis machine which meets the foregoing objects. The machine includes a high performance degassing system wherein water at physiological temperature is fed to a degassing tank that is continuously subjected to a controllable high negative pressure. The pressure is provided by two pumps, one of which draws gas from the tank and another which draws degassed water from the tank. The degassing tank pressure is thus independent of the dialysis solution flow rate.

The dialysis solution pressure and flow rate at the dialyzer are controlled by a pair of flow restrictions which are positioned so as to bracket the dialyzer. In other words, one restriction is upstream and the other downstream of the dialyzer. This permits accurate control of the dialysis solution flow rate and pressure within the dialyzer.

In addition, the proportioning dialysis machine includes a system for sterilizing the interior passageways of the dialysis machine. The sterilizing system includes a heating system for heating water to be flushed through the dialysis machine to a sterilizing temperature, a shunt for bypassing the dialyzer during sterilization, and a valve for permitting recirculating flow of sterilizing water through the proportioning machine.

DESCRIPTION OF THE PREFERRED EMBODIMENT

General

Figure 1:
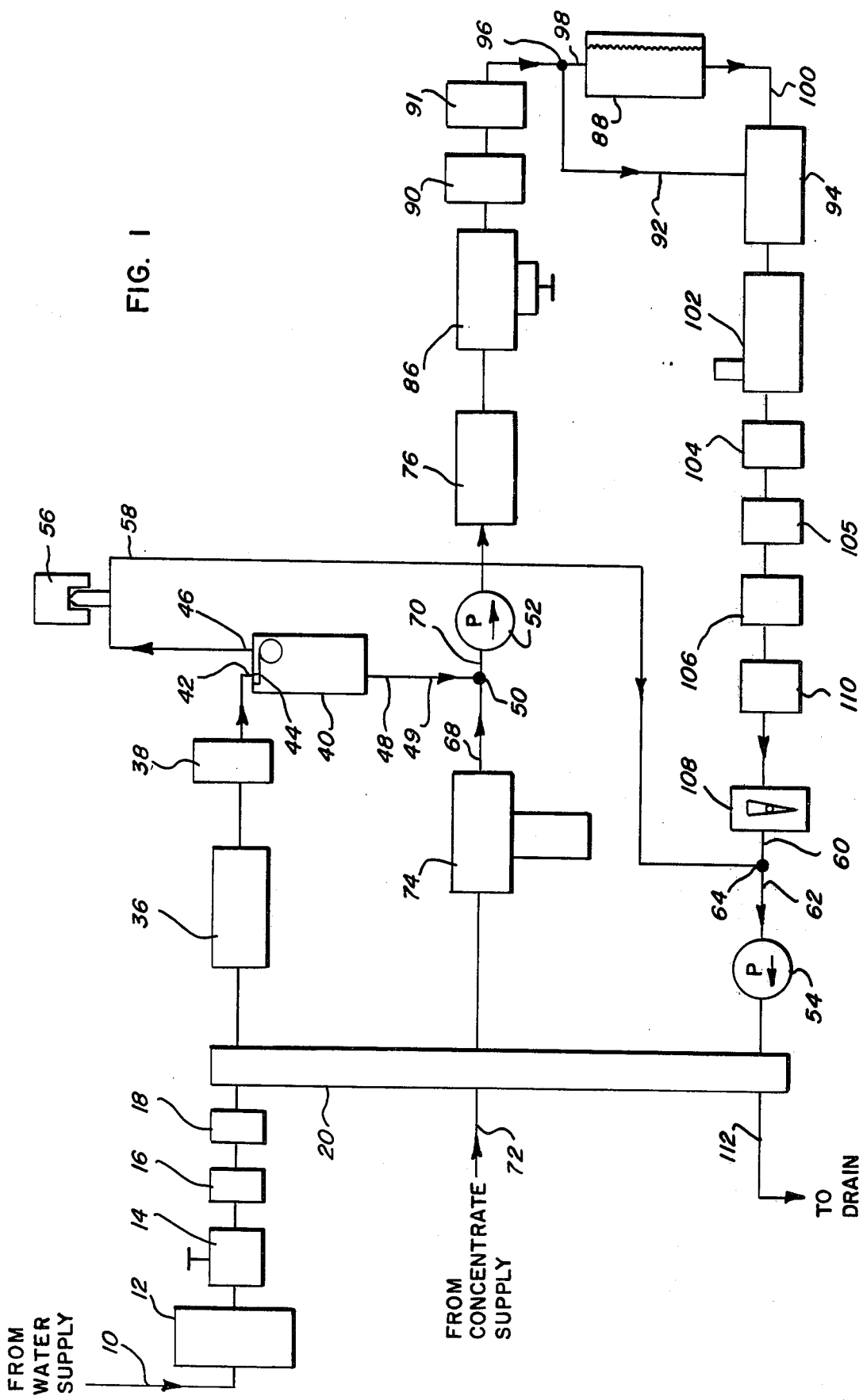
FIG. 1 is a diagrammatic representation of a proportioning dialysis machine.
Figure 2:
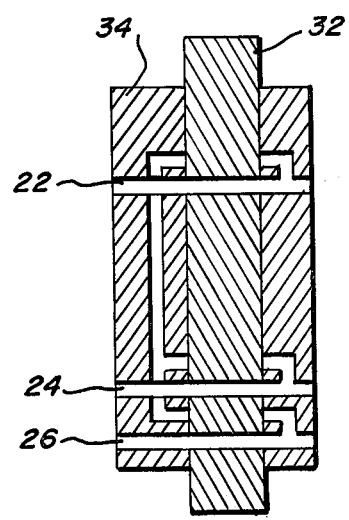
FIG. 2 is a greatly enlarged view of the degassing chamber of this invention.
Figure 3:
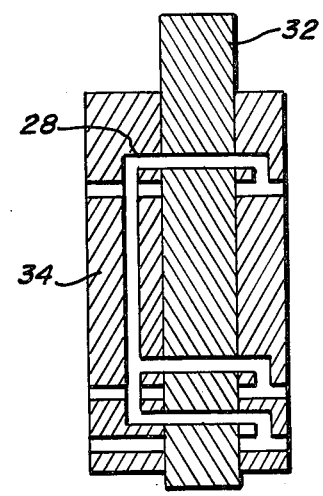
FIG. 3 is an exploded perspective view of a valve used for controlling flow into and out of the proportioning machine.
Figure 4:
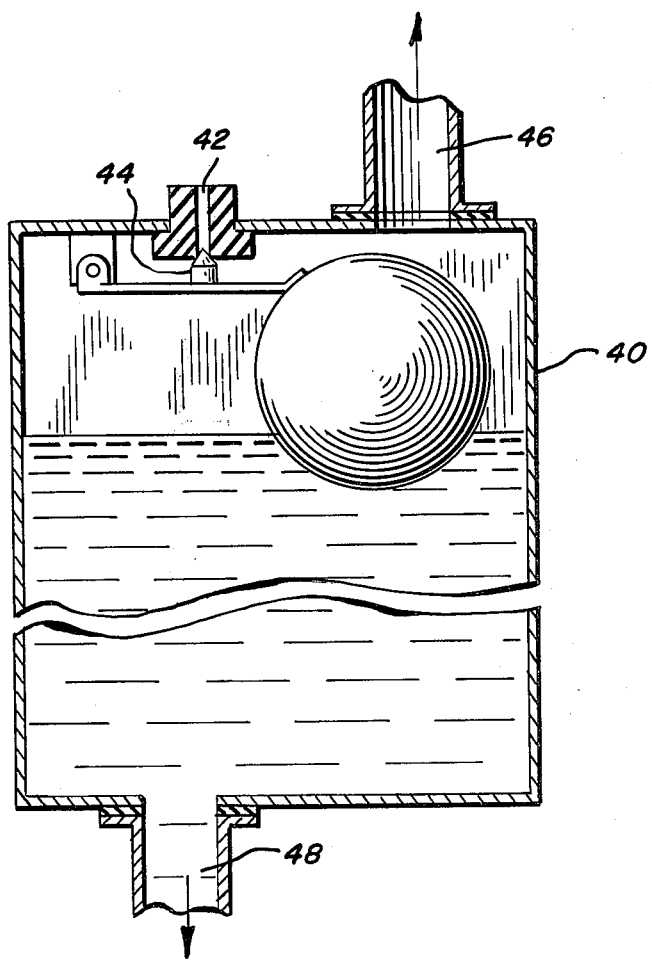
FIG. 4 is a bottom plan view taken substantially along line 4—4 of FIG. 3 and showing various flow ports in one member of the valve.
Figure 5:
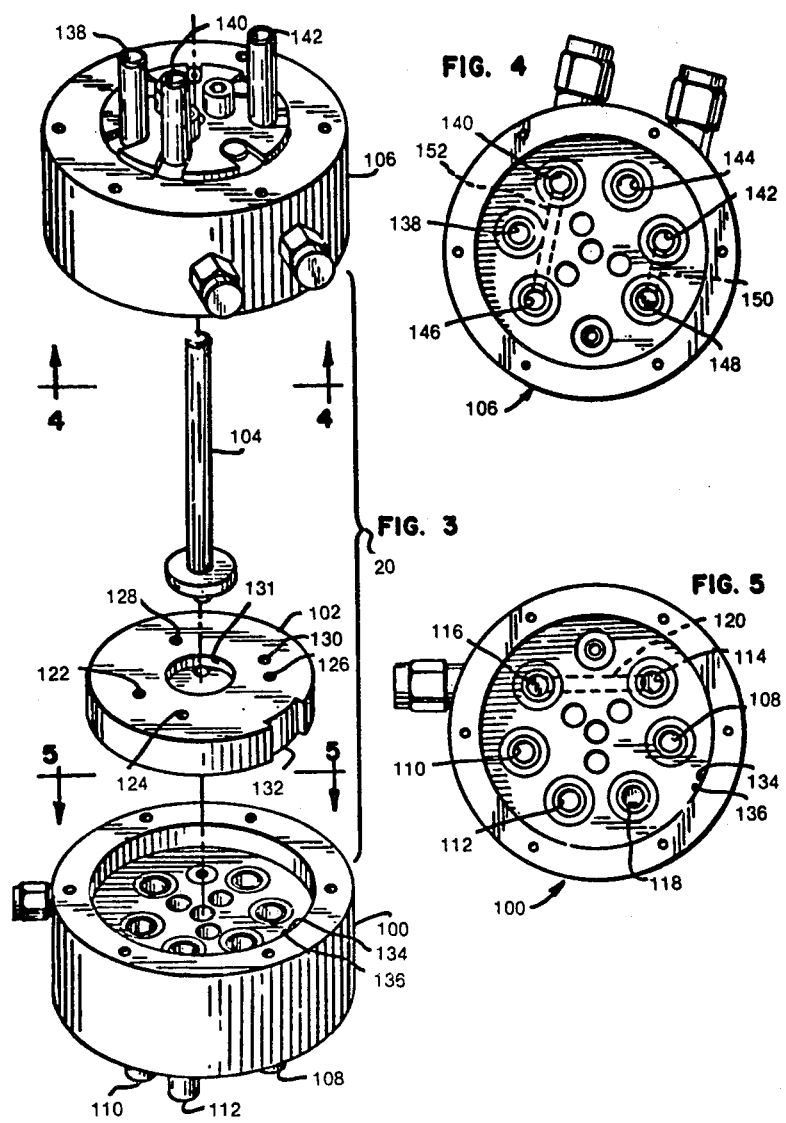
FIG. 5 is a top plan view taken substantially along line 5—5 of FIG. 3 and showing various flow ports in a second member of the valve.

Referring now to FIG. 1, the structure of the proportioning machine will be described with reference to the fluid flow paths therethrough.

Water enters the machine through a water inlet 10 which is connected at its inlet end to a suitable water supply. The water inlet is connected at its outlet end to a filter 12, which removes gross particulate matter. A suitable filter is an AMF cuno cartridge-type filter Model DR200, which removes particles having a diameter greater than 5 microns.

The filtered water passes through a pressure regulator 14 which maintains the water pressure downstream of the regulator at about 15 psi. A pressure gauge 16 measures the water pressure and a water pressure switch or valve 18 is provided downstream of the gauge for preventing water flow into the machine in the event that the pressure at the switch is zero.

The water enters the proportioning machine through the hydraulic valve 20. From the valve 20 water flows through the heater 22 which heats the water to about 37° C. which is referred to as body or physiological temperature. The heated water then flows through the thermistor 24 which monitors and controls the performance of the heater 22. From the thermistor the water flows into a degassing chamber 26 where it is subjected to a high negative pressure. The degassed water is drawn from the degassing chamber to a mixing site 28.

Dialysis solution concentrate flows from a concentrate supply along a concentrate supply line 30 through the valve 20, through a servovalve 32 and from the servovalve to the mixing site 28. At the mixing site the concentrate mixes with the degassed water coming from the degassing chamber 26 so as to form the dialysis solution. The concentrate may be any suitable concentrate, such as Diasol TM 34 hemodialysis bath concentrate sold by Baxter Laboratories. If Diasol TM 34 is used, the dialysis solution is prepared by mixing 34 parts water to 1 part concentrate.

The dialysis solution is drawn along the line 34 to the upstream pump 36. The pump 36 also draws the degassed water from the chamber 26 as well as drawing the concentrate from the concentrate supply. This pump can deliver dialysis solution at a rate of between 300–1000 ml/min. The pressure at the downstream side of the pump is positive and between 0 and 20 psi. The dialysis solution is pumped under the positive pressure to a conductivity cell 38. The conductivity cell measures the conductivity of the dialysis solution which is, in turn, related to the concentration of the concentrate in the solution. A servocircuit between the conductivity cell and servovalve 32 provides means for automatically adjusting the servovalve to increase or decrease the amount of concentrate entering the machine so as to obtain the desired concentration.

The dialysis solution flows from the conductivity cell to a negative pressure regulator 40. The pressure regulator 40 is set so as to automatically control the pressure upstream of the regulator at a desired level in the range from −500 to +200 mm Hg at a flow rate of between 300–1000 ml/min. The solution is then drawn from the negative pressure regulator to a second thermistor 42, which is adapted to provide an alarm in the event that the temperature of the dialysis solution is not at physiological temperatures. A positive pressure switch 44 is provided upstream of the thermistor 42 for preventing further downstream fluid flow in the event the pressure of the dialyzing solution exceeds +200 mm Hg.

A bypass valve 46 is positioned upstream of the positive pressure switch for directing flow either to a dialyzer 48 or along a bypass line 50. The bypass line 50 is connected to a bypass solenoid 52. The dialyzer 48 is connected to the bypass valve 46 by an inlet line 53 and to the bypass solenoid by an outlet line 54. The bypass solenoid diverts the flow of dialysis solution from the dialyzer to the bypass if one of the monitors indicates that the system is not operating properly. For example, there may be a blood leak in the dialyzer or fluid may not be at a physiological temperature. Furthermore, in the sterilization mode described hereinafter the bypass solenoid alternatively diverts the sterilizing fluid through either the bypass line 50 or through the dialyzer inlet and outlet lines 53 and 54 which are connected together in the sterilization mode.

The dialysis solution is drawn from the bypass solenoid 52 to a pressure monitor 56 which provides a means for determining whether or not the pressure in the line at that point is at a predetermined level and to function as an alarm if the pressure is not at the predetermined level.

From the pressure monitor the dialysis solution flows to a sterilization heater 58, an over-temperature switch 60, and a third thermistor 62. The sterilization heater, over-temperature switch and third thermistor do not operate in the dialysis mode but function in the sterilization mode to heat and control the sterilization fluid temperature.

The dialysis solution flows from the thermistor to a blood leak detector 64 which detects the presence of blood in the dialysis solution which could arise from a rupture or leak in the dialyzer membrane. In the event that a blood leak is detected, the bypass solenoid 52 may be activated. From the blood leak detector, the dialysis solution is drawn to a second restriction or flow meter 66 which provides means for monitoring the dialysis solution flow rate and for adjustably controlling the dialysis solution flow rate.

From the flow meter 66, the dialysis solution passes through the line 68 to the junction 70. The line 72 carries the dialysis solution from the junction 70 to the downstream pump 74. From the pump 74, the dialysis solution flows through the valve 20 and via line 76 to the drain.

The degassing chamber 26 is connected to the junction 70 by means of a line 78. A sterilization pressure relief valve 80, which is of the "jiggler" type, is positioned in the line 78 between the degassing chamber 26 and the junction 70. Gas which is removed from the water in the degassing chamber flows via line 78 to the junction 70 under the influence of the downstream pump 74.

The Degassing System

The system for degassing incoming water includes the degassing chamber 26, the upstream pump 36, the downstream pump 74, and the line 78 which connects the degassing chamber to the downstream pump.

The degassing chamber 26 includes a cylindrical tank 26a having a top wall 26b and a bottom wall 26c. The tank is 12 inches high and 4 inches in diameter. The top wall is provided with a gas outlet 26d which is connected to the gas line 78. A second aperture 26e is provided in the top wall and an orifice-defining member 82 is sealingly positioned within the aperture 26e. The member includes a passageway 84, which is adapted to receive water flowing from the thermistor 24 for discharge into the tank.

A float-type check valve assembly 86 is positioned within the chamber. The check valve assembly includes an arm 88 which is hingedly connected at one end to the top wall 26b. A ball-type float 90 is secured to the other end of the arm 88. A conical valving member 92 is secured to the arm and arranged to valvingly engage the outlet end of the orifice passageway 84. In the event the valving member is not in engagement with the orifice but is positioned below the orifice and water flows through the orifice, emerges and flows against the conical member. This causes the water to spray into the tank and also provides greater surface area for degassing.

The bottom wall 26c includes a water outlet aperture 26f through which degassed water is drawn to the junction 28.

In operation water flows into the degassing chamber under the pressure from the water supply. Water continues to flow into the degassing chamber until the water level is sufficient to raise the ball float 90 to a point where the valving member 92 closes off further water flow into the chamber. This defines a minimum gas volume for the chamber and a restricted volume to which a negative pressure is applied.

The downstream pump 74 applies a negative pressure of between −675 and −700 mm Hg. to the gas in the degassing chamber. This pressure is sufficient to remove gas from the gas volume and permit dissolved and entrained gases to leave the water in the degassing tank. At this negative pressure the gas bubbles leave the water and are drawn from the tank through line 78. The downstream pump 74 is a constant speed pump and the negative pressure which it applies to the degassing chamber does not vary with the flow rate. It will also be noted that the downstream pump 74 draws the dialysis solution through the dialyzer 48 from the negative pressure regulator 40. Thus the pump 74 is a dual purpose pump and that is to apply negative pressure to the degassing chamber as well as to draw the dialysis solution through the dialyzer.

Since the water in the degassing tank is under a negative pressure, it must be drawn out from the tank. The upstream pump 36 is also a constant speed pump which draws the degassed water through the outlet 26f from the tank 26. The upstream pump 30 also draws the concentrate from the concentrate supply.

As can be seen from the foregoing, this degassing system provides for efficiently degassing incoming water at a high negative pressure, is capable of degassing water at physiological temperatures and is insensitive to dialysis solution flow rates.

Dialysis Solution Flow Rate and Pressure Controls

It is normally desirable to maintain the dialysis solution pressure within the dialyzer at between −500 and +200 mm Hg and to have the ability to vary the dialysis solution flow rate in the dialyzer between 300-1000 ml/min. The dialysis solution pressure and flow rate in the dialyzer are controlled by the upstream restriction or negative pressure regulator 40; the downstream restriction or flow meter 66; and the downstream pump 74. In the event that the flow meter 66 were open, the pump 74 would act against the negative pressure regulator 40 so as to provide a negative pressure across the dialyzer 48. Positioning of the flow meter 66 between the dialyzer 48 and the downstream pump 74 permits control of the dialysis solution pressure and flow rate in the dialyzer. This is accomplished by adjusting the two restrictions and preferably by adjusting only the upstream restriction 66. Thus, both flow rate and dialysis solution pressure in the dialyzer can be controlled by virtue of the flow meter without requiring changes in the downstream pump 74.

Furthermore, it will be noted that the upstream restriction 66 is positioned downstream of the junction 70 at which the degassing line connects to the spent dialysis solution line. This provides control of the flow rate through the dialyzer independent of the degassing system.

The Sterilization System

The sterilization system includes the valve 20 which closes the system by preventing fresh water from flowing into the system, by preventing fresh concentrate from flowing into the system, and by preventing fluid from draining from the system. The valve also includes internal passages which interconnect the water and the dialysis solution drain line so as to recirculate water therethrough.

In order to sterilize the system, valve 20 is placed in the sterilization or recirculation mode, the bypass solenoid 52 is operated so as to bypass the dialyzer; and the sterilization heater 58, over-temperature switch 60 and the thermistor 62 are activated so as to raise the water in the system to a sterilization temperature of about 120° C. The over-temperature switch is set to deactivate the heater 58 if the water temperature exceeds 140° C. In the sterilization mode, the water heater 22, the first thermistor 24, servovalve 32, the conductivity monitor control 38, the negative pressure regulator 40, and the blood leak detector 64 are inactive. Water is circulated by the action of the pumps 36 and 74 through the water lines, degassing tank 26, the dialysis solution lines and to the downstream pump. Water also flows from the degassing tank through line 78 to the junction 70 and the pump 74. The valve 80 is set to open at 15 psi and acts as a pressure relief valve during sterilization.

From the pump 74 the heated water is then recirculated through the valve 20 back to the water side of the proportioning machine.

Referring to FIGS. 3-7, it will be seen that the valve 20 includes an outlet-side member 100, a diverter shuttle 102, a shuttle control rod 104 and a machine-side member 106. The outlet-side member 100 includes a water inlet port 108, a concentrate inlet port 110, and a drain outlet port 112. In addition to the inlet and outlet passageways, the outlet side member includes three blind passageways 114, 116 and 118. The blind passageways 114 and 116 are interconnected by a cross-hole or passageway 120.

The diverter shuttle 102 is a disc- or puck-shaped member having five flow passageways extending therethrough. The flow passageways include the concentrate flow passage 122, the drain flow passage 124, and the water inlet flow passage 126. In addition, there is provided the drain recirculation passage 128 and the water recirculation passage 130. The diverter shuttle 102 is provided with a center recess 131 for connecting the shuttle to the control rod. A rotation-limiting peripheral notch 132 is also provided which cooperates with a pair of stop pins 134 and 136 in the outlet-side member so as to cooperate in providing alignment of the various passageways described hereinafter.

The shuttle controller 104 is releasably secureable to the shuttle and extends upwardly and sealingly through the dialysis-machine-side member 106. The side member 106 includes a concentrate outlet 138, a drain inlet 140, and a water outlet 142. The member 106 also includes three additional blind passageways 144, 146 and 148. The water outlet passageway 142 is connected to the blind passageway 148 by a cross-hole or passageway 150. The drain inlet 140 is connected to the blind passageway 146 by a cross-hole or passageway 152.

Figure 6:
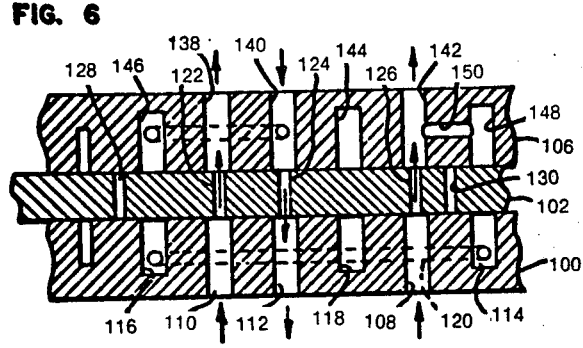
FIGS. 6 and 7 are developed sectional view taken along a line which extends through all flow ports of an assembled valve and show the valve in a full flow open position in FIG. 6 and a closed recirculation position in FIG. 7.

Referring more particularly now to FIG. 6, the shuttle 102 is shown in the flow-through mode. In that mode water flows through the inlet 108, the passage 126 and out the outlet 142 into the water side of the dialysis machine. Concentrate flows through the inlet 110, through the passage 122 and out the outlet 138 to the servovalve 32. Fluid flowing from the pump 74 passes through the drain inlet 140, through the passageway 124 and to drain through the outlet 112.

Figure 7:
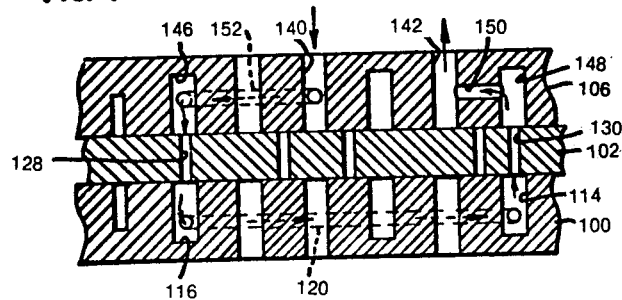

The sterilization mode is shown in FIG. 7. In this mode the diverter shuttle has been rotated so that the water recirculation passage 130 is aligned with the blind passages 148 and 114. The drain recirculation passageway 128 is aligned with the blind passageways 146 and 116. All other passageways are blocked by the shuttle 102.

Heated sterilizing water flowing from the downstream pump 74 enters the valve 20 via the drain inlet 140. Since the passageway is blocked, the water then flows through the drain cross-hole 152 to the blind passageway 146. From the blind passageway 146, the water flows through the shuttle passage 128 into the outlet-side blind passage 116. From the outlet-side blind passage 116, the water flows through the outlet-side cross-hole 120 to the outlet-side blind passage 114. From the outlet blind passage 114, the water flows through the shuttle passage 130 to the dialysis-side blind passage 148. From there the water flows through the cross-hole 150 and out the water outlet 142. Thus by operation of the valve water from the dialysis solution or drain line flows through the valve and back to the water side of the proportioning machine for sterilization of the internal portions of the dialysis machine.

It should be noted that the concentrate supply lines are not sterilized by recirculating hot water through the lines in the servovalve. The reason is that the concentrate lines from the valve to the junction 28 are deemed to be sterile by virtue of the fact that the concentrate fluid itself is sterile.

It will be appreciated that numerous modifications and changes can be made to the embodiment disclosed herein without departing from the spirit and scope of this invention.

What is claimed is:

1. A dialysis machine which constantly delivers dialysis solution to a dialyzer during dialysis, and which includes a degassing system for removal of dissolved and entrained gases from a substantially body temperature liquid said system including:
   chamber means for receiving said liquid for treatment and having: liquid inlet means, liquid outlet means in a lower portion of said chamber, and gas outlet means in an upper portion of said chamber means; and
   means for producing a negative pressure within said chamber means,
wherein the improvement comprises:
   there being provided valve means associated with said chamber means and cooperating with said liquid inlet means for controlling liquid flow into said chamber means and the liquid level within said chamber so as to establish a restricted volume for gas within said chamber;
   said means for producing a negative pressure in said chamber being first pump means connected to said gas outlet means for drawing gas from the restricted volume for gas within said chamber; and
   said chamber means, valve means and first pump means cooperating to controllably produce negative pressures in said chamber as low as about −700 mm/Hg.

2. A dialysis machine as in claim 1, wherein said chamber means, valve means and said first pump means cooperate substantially independently of dialysis solution flow rates through a dialyzer to produce negative pressures within said chamber.

3. A dialysis machine as in claim 1, wherein said liquid inlet means is positioned in an upper portion of said chamber means and the level of said liquid is maintained at a level below the liquid inlet means.

4. A dialysis machine as in claim 3, wherein said valve means includes:
   elongated arm means with one end hingedly connected to said chamber means,
   float member means secured to the other end of said arm for cooperation with said liquid; and
   valving means secured to said arm intermediate its ends and arranged to cooperate with said liquid inlet means to open and close said inlet means in response to changes in the liquid level.

5. A dialysis machine as in claim 4 wherein said valving means includes a conically-shaped tip adapted to close said liquid inlet means in one position and adapted to cause liquid flowing into said chamber to disperse into a spray.

6. A dialysis machine as in claim 1, which further includes second pump means connected to said liquid outlet means for drawing degassed liquid from said chamber means through said liquid outlet means.

7. A dialysis machine as in claim 6, wherein said second pump means is a positive pressure pump and the liquid pressure on the downstream side of said pump is positive.

8. A dialysis machine as in claim 6, wherein said liquid is water and there is further provided, in combination therewith, supply means for a concentrate to be mixed with said water for preparing a dialysis solution; and mixing means operatively associated with said concentrate supply means, said liquid outlet means, and the upstream side of said second pump means for mixing concentrate and degassed water.

9. A dialysis machine as in claim 6, and in combination therewith, a dialyzer operatively associated with the upstream side of said first pump means and operatively associated with the downstream side of said second pump means.

10. A dialysis machine as in claim 9, wherein said dialyzer receives at least a portion of the liquid pumped between said first pump means and said second pump means.

11. A dialysis machine as in claim 9, wherein there is provided means defining a liquid flow path for connecting said chamber means, said second pump means, said dialyzer means, and said first pump means.

12. A dialysis machine as in claim 6, wherein there is further provided a liquid flow path to which said second pump means and said first pump means are connected so that the downstream side of said second pump means is associated with the upstream side of said first pump means.

13. A dialysis machine as in claim 1, wherein said first pump means is operatively associated with a dialyzer for drawing dialysis solution through the dialyzer, and in combination therewith, a system to control the pressure and flow rate of dialysis solution within the dialyzer, said system including:

adjustable restriction means positioned upstream of the dialyzer and adapted for operative association with a dialysis solution inlet to the dialyzer;

adjustable restriction means positioned downstream of the dialyzer and adapted for operative association with a dialysis solution outlet from the dialyzer, and said downstream restriction means also being positioned upstream of said first pump means and being operatively associated with said first pump means; and said upstream restriction means and said downstream restriction means adapted for adjustment so as to control the dialysis solution pressure and flow rate within the dialyzer.

* * * * *